United States Patent [19] [11] 4,052,212
Deguchi et al. [45] Oct. 4, 1977

[54] PHOTOGRAPHIC SILVER HALIDE EMULSION CONTAINING 2-EQUIVALENT CYAN COUPLER

[75] Inventors: Hidetaka Deguchi; Hajime Wada; Takaya Endo; Shoji Kikuchi; Haruo Hori, all of Hino, Japan

[73] Assignee: Konishiroku Photo Industry Co., Ltd., Tokyo, Japan

[21] Appl. No.: 547,405

[22] Filed: Feb. 5, 1975

[30] Foreign Application Priority Data

Feb. 8, 1974 Japan .................................. 49-16057

[51] Int. Cl.² ................................................ G03C 7/00
[52] U.S. Cl. ........................................ 96/56.2; 96/55; 96/100 R
[58] Field of Search .......................... 96/100, 55, 56.2

[56] References Cited

U.S. PATENT DOCUMENTS

| 2,772,161 | 11/1956 | Loria et al. | 96/100 |
| 3,432,521 | 3/1969 | Loria | 96/100 |
| 3,516,831 | 6/1970 | Wolf et al. | 96/100 |

*Primary Examiner*—J. Travis Brown
*Attorney, Agent, or Firm*—Haseltine, Lake & Waters

[57] ABSTRACT

Cyan couplers of the 2-equivalent type, useful in photography are described. These compounds are characterized in that they have at least one divalent group of the formula, $-OCH_2CO-$, in the molecule with a split-off group at the methoxy site of said divalent radical. Photographic materials and color developers incorporating these couplers are also described.

5 Claims, No Drawings

PHOTOGRAPHIC SILVER HALIDE EMULSION CONTAINING 2-EQUIVALENT CYAN COUPLER

This invention relates to a novel coupler for use in the photography, and particularly to a novel cyan coupler employed in the photography using siler halides as photosensitive components.

In the photography, a silver halide has frequently been used as a photosensitive component for light-information recording because of its being excellent in photographic properties such as sensitivity, gradation, etc. In order to obtain a color image by using a silver halide as the photosensitive component, it has been a general practice to use the silver halide in combination with a certain color-forming compound and to react said color-forming compound with a certain reactive compound to form a dye in response to the information recorded on the silver halide, thereby obtaining a dye image. The said color-forming compound is a coupler, while the said reactive compound used for dye formation in combination with said coupler is, in general, a color developing agent, e.g. an aromatic primary amine type developing agent.

As is well known, when silver halide which has been exposed by light along the information is developed with a color developing agent in the presence of a coupler, the color developing agent reduces the silver halide to developed silver and, at the same time, is oxidized by itself to form an active oxidation product of the color developing agent, which oxidation product reacts with the coupler to form a dye, with the result that a dye image is formed in response to the information recorded on the silver halide. The reaction of the coupler with the color developing agent is effected at the active point of the coupler, and the active point is, in general, in the active methine or methylene group in the coupler molecule.

A coupler having a hydrogen atom in the active point is called a 4-equivalent coupler, while a coupler having in the active point a so-called split-off group, which is easily released in the reaction with the color developing agent, is called a 2-equivalent coupler.

At the time of reaction with the color developing agent, the 4-equivalent coupler requires 4 equivalents of development center of exposed silver halide, while the 2-equivalent coupler requires 2 equivalents of development center. Generally, therefore, the 2-equivalent coupler gives a dye image higher in density when the amount of developed silver is same. Further, when the group at the linking portion (bond group) of the split-off group linked to the active point of the 2-equivalent coupler is properly selected, the 2-equivalent coupler imparts a development-inhibiting action to a compound formed when the split-off group has been released. For example, a 2-equivalent coupler containing a split-off group having a thio group (—S—) as the bond group is called a development inhibitor-releasing type coupler (D.I.R. coupler), and can be applied variously since it inhibits the development in proportion to the amount of developed silver. For example, the D.I.R. coupler not only displays various effects, e.g. so-called intra-image effects within layers such as control of image tone, fine granulation of image, etc. and so-called inter image effects such as improvement in hue by acting on other layers, but also is applicable to diffusion transfer type photographic materials, taking advantage of its action on other layers.

Further a certain 2-equivalent coupler, e.g. a coupler which has a split-off group incorporated with a dye moiety and hence can form a diffusible dye on an image-receiving layer, utilizing the dye released from the split-off group, is also applicable to diffusion transfer type photographic material. This kind of coupler is called a diffusible dye-releasing type coupler (D.D.R. coupler). Still further, a certain colored 2-equivalent coupler has a masking effect for color compensation of color image, and this kind of coupler is called a colored coupler.

As mentioned above, the 2-equivalent coupler is essentially excellent and is applicable to various purposes as compared with the 4-equivalent coupler, and hence tends to be more frequently used.

However, the conventional 2-equivalent coupler is insufficient in color-forming speed, despite of its being more excellent in properties than the 4-equivalent coupler. Further, the 2-equivalent coupler has such disadvantages that it tends to fog or stain a silver halide-containing photosensitive layer, or cannot be dispersed in a photosensitive layer with a sufficient dispersion density. Accordingly, the dismissal of the above-mentioned disadvantages has been desired.

A principal object of the present invention is to provide a novel 2-equivalent coupler which has been free from the above-mentioned disadvantages.

Another object of the invention is to provide a 2-equivalent cyan coupler excellent in photographic properties.

A further object of the invention is to provide a light-sensitive silver halide photographic material and a photograph process using the said 2-equivalent cyan coupler.

Concretely, the present invention is concerned with a photographic 2-equivalent cyan coupler having at the active point of the cyan coupler a split-off group having as the linking portion a divalent group of the general formula (I),

$$—OCH_2CO— \qquad (I)$$

said divalent group having its methoxy moiety on the active point side of cyan coupler.

The above-mentioned 2-equivalent cyan coupler has a so-called carbonyl methoxy linkage and, due to this linkage, is high in color-forming speed, gives no fog nor color stain to any photosensitive layer, and is favorably dispersible to a high density in photosensitive and the like constitutive layers of a photographic material. Further, a dye formed from the said cyan coupler is excellent in fastness to light, heat and humidity, has excellent light absorption characteristics showing sharp absorptions without any useless light absortions, and shows no such development-inhibiting property as shown by a certain conventional 2-equivalent coupler.

The 2-equivalent cyan coupler of the present invention has many such advantages that when it is incorporated into a light-sensitive silver halide photographic material, the photosensitive layer can be made thinner, so that the resulting color image can be enhanced in resolution and sharpness, and, particularly when incorporated into a multi-layered photographic material, the photographic material is improved in light permeability to lower layers and thus is enhanced in photographic properties.

More concretely, the 2-equivalent cyan coupler of the present invention may typically be represented by the general formula (II) or (III),

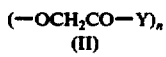 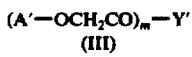

wherein A is an n-valent cyan coupler residue; A' is a monovalent cyan coupler residue; Y is a monovalent organic group; Y' is an m-valent organic group; and n and m are individually a positive integer.

A coupler of the general formula (II) or (III) is a typical and fundamental type of the 2-equivalent cyan coupler of the present invention. A 2-equivalent coupler composed of a mixture of couplers of the general formulas (II) and (III) is also useful in the present invention. In the above-mentioned general formulas (II) and (III), the cyan coupler residue is a residue formed by removing the hydrogen atom or split-off group at the active point of cyan coupler. In case the coupler has a plurality of active points in one molecule, split-off groups to be introduced into the individual active points may be same or different, or the active points may have partly been incorporated with hydrogen atoms. Preferably, however, all the active points have been incorporated with the split-off groups according to the present invention.

In the above-mentioned general formulas (II) and (III), preferable as the group Y are aliphatic hydrocarbon residues, aromatic hydrocarbon residues, heterocyclic residues, alkoxy groups, phenoxy groups, naphthoxy groups, aliphatic hydrocarbon amino residues, heterocyclic amino residues and mercapto groups, which groups includes those having substituents; preferable as the group Y' are m-valent aliphatic hydrocarbon residues, aromatic hydrocarbon residues, heterocyclic residues, alkylenedioxy groups, arylenedioxy groups, alkylenediamino residues, arylenediamino residues and heterocyclic diamino residues, and are m-valent groups formed by mutual linking of said groups, which groups include those having substituents, e.g. compounded divalent groups in which divalent aliphatic hydrocarbon residues have linked to arylene groups, and the linked state thereof may be such that k groups (k is a positive integer) selected from divalent aliphatic hydrocarbon residues have linked in block-wise manner or randomly to 1 group (1 is a positive integer) selected from arylene groups. Further, the said m-valent groups may have oxygen atoms, imino groups, etc. at the terminals, and the two adjacent carbon atoms of the m-valent groups may have been divided by any of oxygen atoms, sulfur atoms, imino groups, sulfonyl groups, carbonyloxy groups, aminocarbonyl groups, sulfonamide groups, etc.; and n and m are preferably 1 or 2, but may be 3 or more in case a cyan coupler known as a polymer coupler is used as the matrix.

Typical as desirable couplers of the present invention are those having cyan coupler residues represented by the below-mentioned general formula (IV), (V) or (VI).

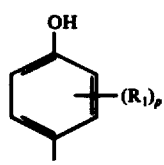

(IV)

(V)

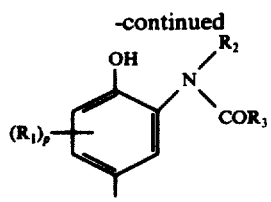

(VI)

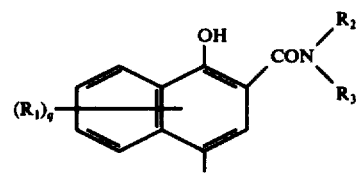

wherein $R_1$ is a hydrogen atom, a halogen atom, an aliphatic hydrocarbon residue, $-O-R_4$ or $-S-R_4$ (where $R_4$ is an aliphatic hydrocarbon residue), and in case two or more $R_1$ are present in one molecule, these may be same or different, said aliphatic hydrocarbon residue including those having substituents; $R_2$ and $R_3$ are individually a group selected from aliphatic hydrocarbon residues, aryl groups and heterocyclic residues, or either one of them may be a hydrogen atom, said group including those having substituents, and $R_2$ and $R_3$ may form in combination a nitrogen-containing hetero ring; p is an integer of 1 to 4 (provided that in the general formula (V), p is an substituents, of 1 to 3); and q is an integer of 1 to 5. The aliphatic hydrocarbon residues may be any of those which have been saturated or unsaturated, and any of those which are straight chain, branched-chain or cyclic. Preferably, they are alkyl groups such as, for example, methyl, ethyl, isobutyl, dodecyl, octadecyl, cyclobutyl and cyclohexyl groups, or alkenyl groups such as, for example, allyl groups. Typical as the aryl groups are phenyl and naphthyl groups, and typical as the heterocyclic residues are pyridyl, quinolyl, thienyl, piperidyl and imidazolyl groups. The substitutents, which are to be introduced into said aliphatic hydrocarbon residues, aryl groups and heterocyclic residues, include halogen atoms, nitro groups, hydroxyl groups, carboxyl groups, amino groups, substituted amino groups, sulfo groups, alkyl groups, substituted alkyl groups, alkenyl groups, aryl groups, heterocyclic residues, alkoxy groups, aryloxy groups, arylthio groups, arylazo groups, acylamino groups, carbamoyl groups, ester groups, acyl groups, acyloxy groups, sulfonamide groups, sulfamoyl groups, sulfonyl groups morpholino groups, piperazyl groups and imidazolyl groups. Further, the hetero ring to be formed by $R_2$ and $R_3$ is preferably a nitrogen-containing hetero ring used as the above-mentioned heterocyclic residue.

In the aforesaid general formulas (II) and (III), the aliphatic hydrocarbon residues may be any of those which have been saturated or unsaturated, and any of those which are straight chain, branched-chain or cyclic. For example, monovalent aliphatic hydrocarbon residues are typically alkyl and alkenyl groups, and are preferably methyl, ethyl, isobutyl, octyl, 1-octyl, octadecyl, cyclobutyl, cyclohexyl and 2-norbornyl groups; and divalent aliphatic hydrocarbon residues are typically alkylene groups, and are preferably methylene, ethylene, butylene and hexylene groups. The aromatic hydrocarbon residues are typically aryl and arylene groups, and are preferably phenyl, naphthyl, phenylene and naphthylene groups. The heterocyclic residues are preferably residues of 5- or 6-membered heterocyclic rings containing heterocyclic ring atoms such as nitrogen, sulfur or oxygen atoms, and are desirably monovalent groups such as thienyl, pyridinyl, quinolyl and oxadiazolyl groups or divalent groups such as pyridinylene and quinolylene groups. The acyl groups are desirably acetyl, benzoyl and thioacetal groups; the thioacyl groups are preferably thioacetyl, thiobenzoyl and thionaphthoyl groups; and the sulfonyl groups are, for example, phenylsulfonyl, chlorosulfonyl and methanesulfonyl groups.

The various groups, which are used as the groups Y and Y' in the general formulas (II) and (III), include those having substituents, as mentioned previously, and typical as such substituents are same as those used in the general formula (IV), (V) and (VI).

Concrete examples of the split-off group having as the bond group a divalent group represented by the aforesaid general formula (I) are shown below.

Methylcarbonyl methoxy group

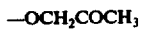

Ethylcarbonyl methoxy group

Methoxycarbonyl methoxy group

Ethoxycarbonyl methoxy group

Butoxycarbonyl methoxy group

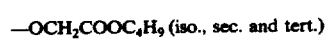

Dodecyloxycarbonyl methoxy group

—OCH$_2$COOC$_{12}$H$_{25}$

Ethylaminocarbonyl methoxy group

Diethylaminocarbonyl methoxy group

Laurylaminocarbonyl methoxy group

Benzylcarbonyl methoxy group

Benzylaminocarbonyl methoxy group

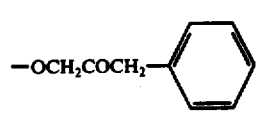

Benzoyl methoxy group

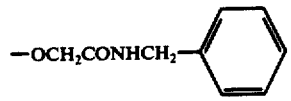

Phenoxycarbonyl methoxy group

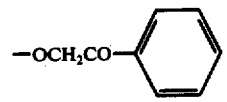

Anilinocarbonyl methoxy group

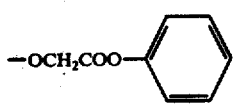

α-Naphthylcarbonyl methoxy group

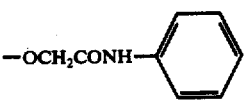

α-Naphthyloxycarbonyl methoxy group

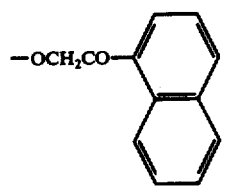

β-Naphthylaminocarbonyl methoxy group

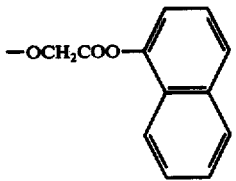

4-Nitrophenylcarbonyl methoxy group

−OCH₂CO—⟨C₆H₄⟩—NO₂

4-Chlorophenylcarbonyl methoxy group

−OCH₂CO—⟨C₆H₄⟩—Cl

4-Methylphenylcarbonyl methoxy group

−OCH₂CO—⟨C₆H₄⟩—CH₃

4-Nitrophenoxycarbonyl methoxy group

−OCH₂COO—⟨C₆H₄⟩—NO₂

4-Chlorophenoxycarbonyl methoxy group

−OCH₂COO—⟨C₆H₄⟩—Cl 2,4-Dimethylphenoxycarbonyl methoxy group

−OCH₂COO—⟨C₆H₃⟩(CH₃)(CH₃)

4-Dodecylbenzoyl methoxy group

−OCH₂CO—⟨C₆H₄⟩—C₁₂H₂₅

4-Aminobenzoyl methoxy group

−OCH₂CO—⟨C₆H₄⟩—NH₂

4-Aminophenoxycarbonyl methoxy group

−OCH₂COO—⟨C₆H₄⟩—NH₂

4-Aminophenylaminocarbonyl methoxy group

−OCH₂CONH—⟨C₆H₄⟩—NH₂

4-Lauroylamidophenoxycarbonyl methoxy group

−OCH₂COO—⟨C₆H₄⟩—NHCOC₁₁H₂₃

4-Stearoylamidophenylamino methoxy group

−OCH₂CONH—⟨C₆H₄⟩—NHCOC₁₇H₃₅

4-(2-Hydroxy-5-sodium-sulfophenylazo)phenoxycarbonyl methoxy group

−OCH₂COO—⟨C₆H₄⟩—N=N—⟨C₆H₃⟩(OH)(SO₃Na)

4-(2-Hydroxy-5-sodium-sulfophenylazo)anilinocarbonyl methoxy group

−OCH₂CONH—⟨C₆H₄⟩—N=N—⟨C₆H₃⟩(OH)(SO₃Na)

Ethylenedioxybiscarbonyl methoxy group

OCH₂COOCH₂CH₂OCOCH₂O—

Ethylenediaminobiscarbonyl methoxy group

—OCH₂CONHCH₂CH₂NHCOCH₂O—

4,4′-Methylenebisphenoxycarbonyl methoxy group

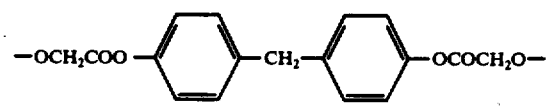

4,4'-Methylenebisanilinocarbonyl methoxy group

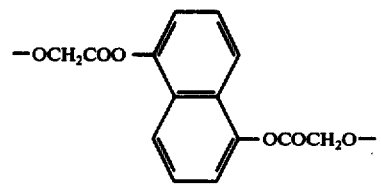

1,5-Naphthalanebisaminocarbonyl methoxy group

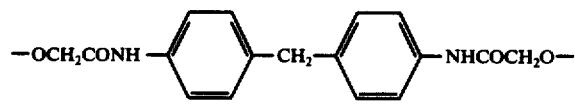

1,4-Phenylenebiscarbonyl methoxy group

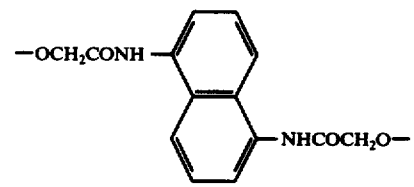

4,4'-Diphenyloxycarbonyl methoxy group

1,4-Phenylenebisoxycarbonyl methoxy group

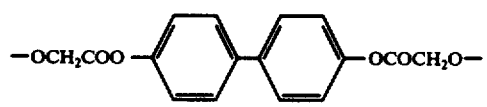

4,4'-Diphenylbisaminocarbonyl methoxy group

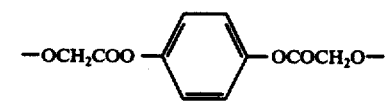

1,4-Phenylenebisaminocarbonyl methoxy group

4-Quinolyloxycarbonyl methoxy group

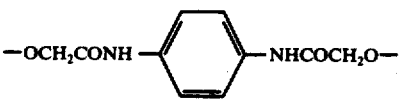

1,3-Phenylenebisoxycarbonyl methoxy group

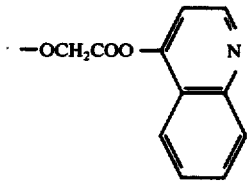

2-Quinolylaminocarbonyl methoxy group

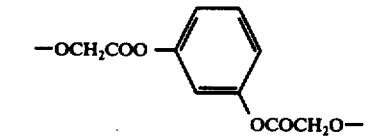

1,3-Phenylenebisaminocarbonyl methoxy group

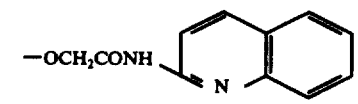

Chloromethylcarbonyl methoxy group

—OCH$_2$COCH$_2$Cl

Chloroethoxycarbonyl methoxy group

—OCH$_2$COOCH$_2$CH$_2$Cl

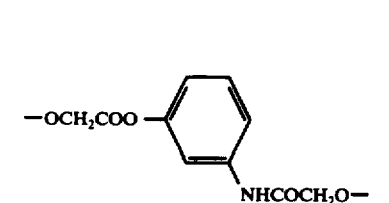

1,5-Naphthalenebisoxycarbonyl methoxy group

Chloroethylaminocarbonyl methoxy group

—OCH$_2$CONHCH$_2$CH$_2$Cl

N-Methylanilinocarbonyl methoxy group

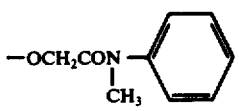

Phenylthiocarbonyl methoxy group

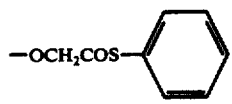

Benzenesulfonylaminocarbonyl methoxy group

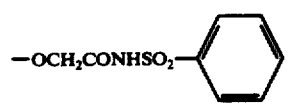

1,4-Phenylenebiscarbonyloxycarbonyl methoxy group

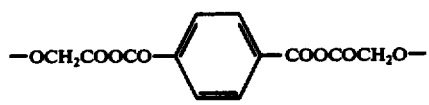

1,3-Phenylenebissulfonylaminocarbonyl methoxy group

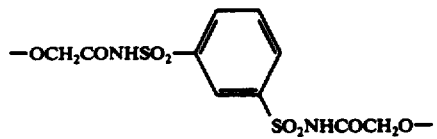

Couplers having such split-off groups as shown above at the active centers of cyan couplers represented by, for example, the aforesaid general formula (IV), (V), or (VI) are successfully used in the present invention. It is considered that the excellent properties of the photographic couplers of the present invention are ascribable to the said bond groups.

Concrete examples of typical couplers according to the present invention are enumerated below, but couplers of the present invention are not limited to these.

1. 1-Hydroxy-4-benzoylmethoxy-N-[δ-(2,4-di-tert-amylphenoxy)butyl]-2-naphthamide

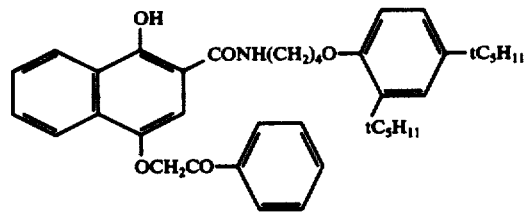

2. 1-Hydroxy-4-anilinocarbonylmethoxy-N-[δ-(2,4-di-tert-amylphenoxy)butyl]-2-naphthamide

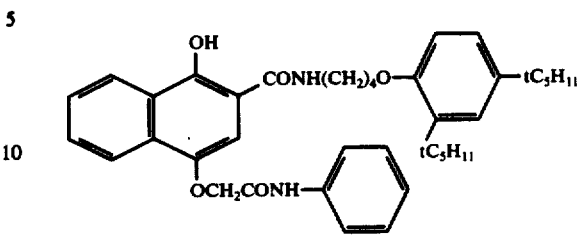

3. 1-Hydroxy-4-phenoxycarbonylmethoxy-N-[δ-(2,4-di-tert-amylphenoxy)butyl]-2-naphthamide

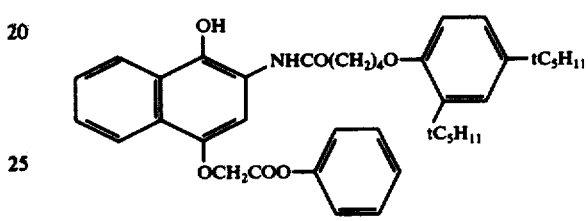

4. 1-Hydroxy-4-(4-nitrophenoxycarbonylmethoxy)-N-[δ-(2,4-di-tert-amylphenoxy)butyl]-2-naphthamide

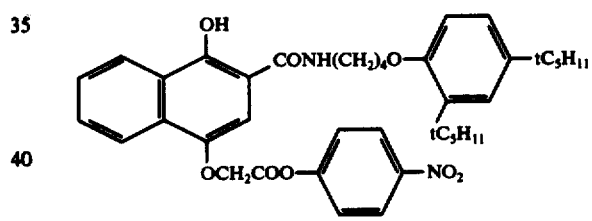

5. 1,2-Bis-[4-hydroxy-3-[N-[δ-(2,4-di-tert-amylphenoxy)butyl]carbonyl]-1-naphthyloxyacetamido]-ethane

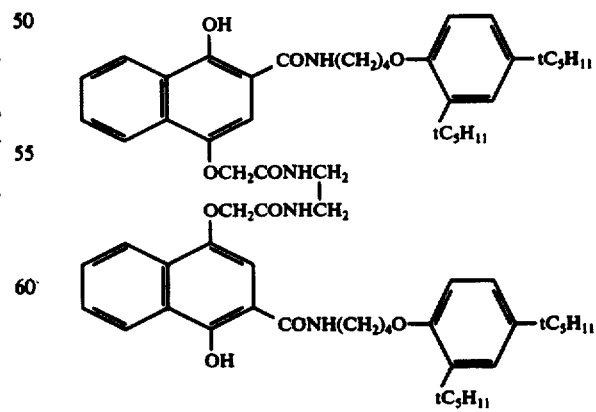

6. 1-Hydroxy-4-(4-chlorobenzoylmethoxy)-n-dodecyl-2-naphthamide

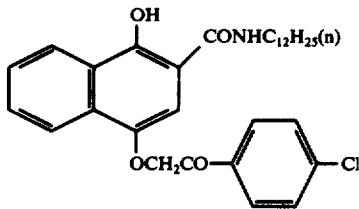

7. Disodium salt of 1-hydroxy-4-[4-(1-hydroxy-3,6-disulfo-2-naphthylazo)-phenoxycarbonylmethoxy]-n-dodecyl-2-naphthamide 9. 1-Hydroxy-4-benzylaminocarbonyl-methoxy-N-[δ-(3-n-dodecyloxyphenoxy)butyl]-2-naphthamide

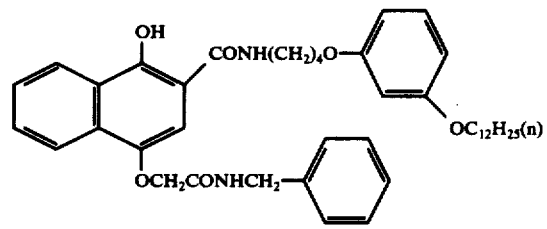

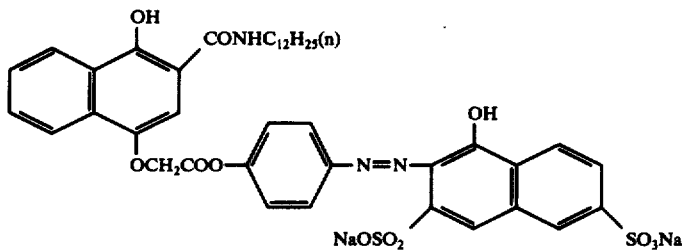

8. 1,3-Bis-(4-hydroxy-3-n-dodecylcarbamoyl-1-naphthyloxyacetamido)benzene

10. Disodium salt of 1-hydroxy-4-[4-(2-hydroxy-3,6-disulfo-1-naphthylazo)anilinocarbonylmethoxy]-N-[δ-(3-n-dodecyloxyphenoxy)butyl]-2-naphthamide

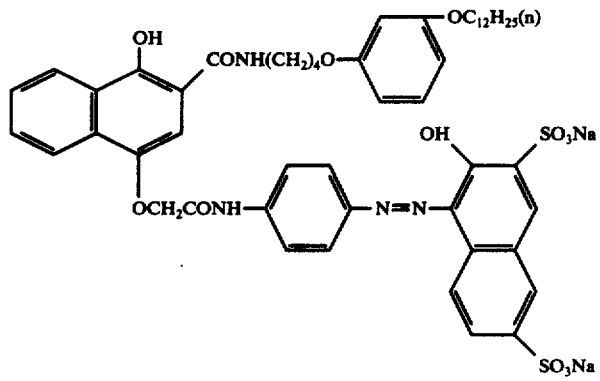

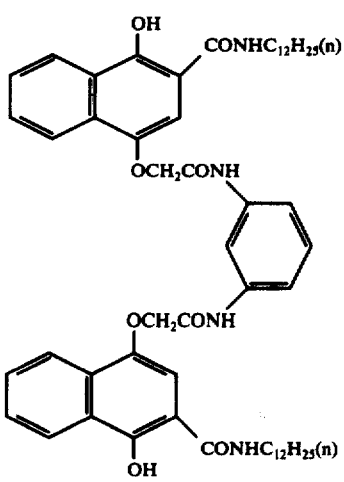

11. 1-Hydroxy-4-(ethoxycarbonylmethoxy)-N-[δ-(2,4-di-tert-amylphenoxy)butyl]-2-naphthamide

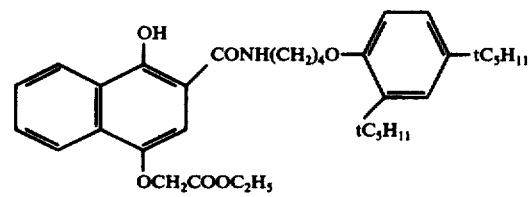

12. 1-Hydroxy-4-ethylaminocarbonylmethoxy-N-[β-(4-n-lauroylamidophenyl)ethyl]-2-naphthamide

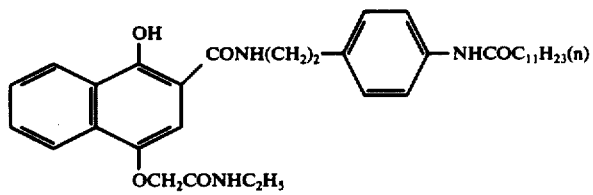

13. Bis[4-[4-hydroxy-3-[N-[β-(4-n-lauroylamido-phenyl)ethyl]carbamoyl]-1-naphthyloxyacetyloxy]-phenyl]-methane

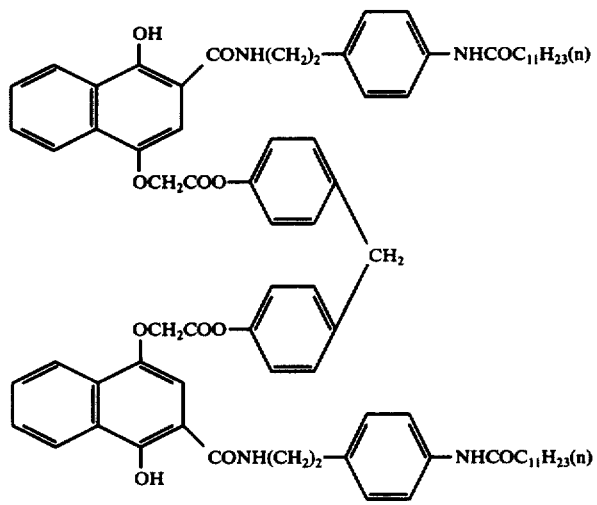

14. 1-Hydroxy-4-(anilinocarbonylmethoxy)-N-n-octadecyl-N-(3,5-dicarboxyphenyl)-2-naphthamide

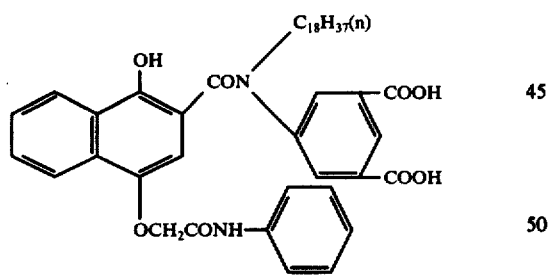

15. 1-Hydroxy-4-ethoxycarbonylmethoxy-N-[β-(β-carboxy-β-n-octadecylpropionoylamino]ethyl-2-naphthamide

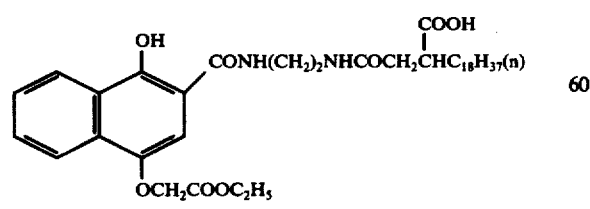

16. Potassium salt of 1-hydroxy-4-n-dodecylaminocarbonylmethoxy-N-ethyl-N-sulfoethyl-2-naphthamide

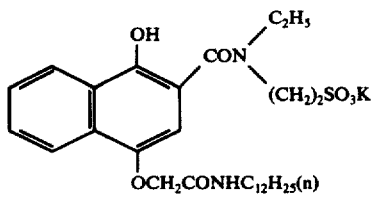

17. 1-Hydroxy-4-(4-lauroylamido)-phenoxycarbonylmethoxy-N-ethyl-N-(3,5-dicarboxyphenyl)-2-naphthamide

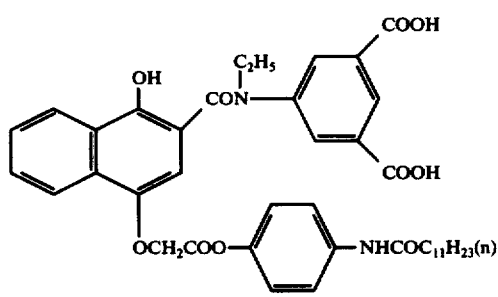

18. 1-Hydroxy-4-(N-ethylanilinocarbonylmethoxy)-N-ethyl-N-(3,5-dicarboxyphenyl)-2-naphthamide

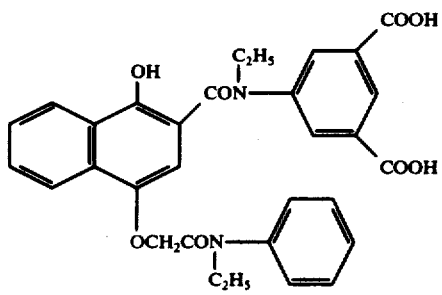

19. 1-Hydroxy-4-anilinocarbonylmethoxy-2-naphthomorpholide

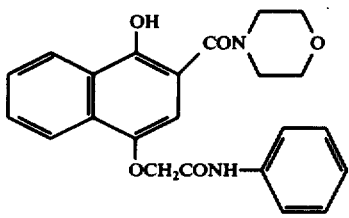

20. 1,4-Phenylenebis-(1-hydroxy-4-anilinocarbonylmethoxy-2-naphthamide)

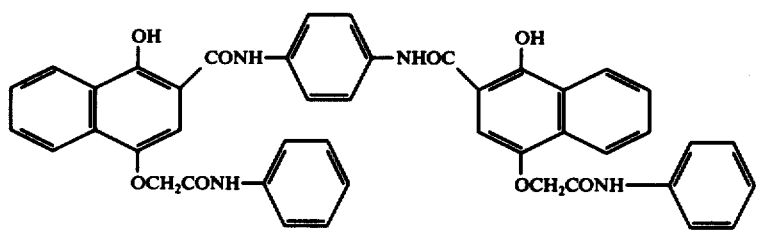

21. 6-Chloro-5-methyl-4-phenoxycarbonylmethoxy-2-acetaminophenol

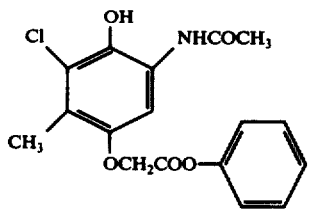

22. 1-Hydroxy-4-phenylthiocarbonylmethoxy-N-[δ-(2,4-di-tert-amylphenoxy)butyl]-2-naphthamide

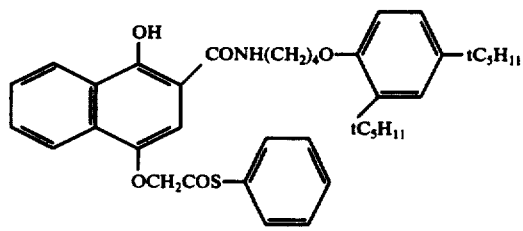

23. 1-Hydroxy-4-(4-aminoanilinocarbonylmethoxy)-N-(2-n-tetradecyloxyphenyl)-2-naphthamide

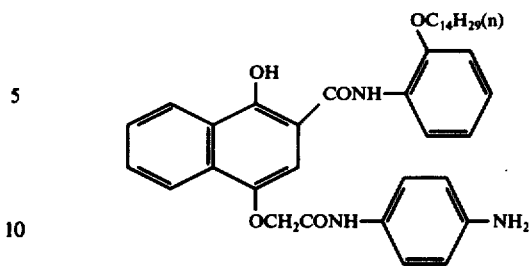

The above-mentioned couplers of the present invention can be synthesized in the following manner:

For example, a naphthol type coupler is synthesized by the method disclosed in Journal of the American Chemical Society, Vol. 64, page 798 (1942) in such a manner that 1,4-dihydroxy-2-naphthoic acid is reacted in a solvent such as acetone or DMF in the presence of pyridine, sodium carbonate or sodium hydroxide at room temperature or at an elevated temperature with a corresponding halogenated methylcarbonyl group-containing compound, e.g. ethyl chloroacetate ester, phenacyl bromide, chloroacetic acid anilide or phenyl chloroacetate to obtain a naphthoic acid, e.g. 1-hydroxy-4-ethoxycarbonylmethoxy-2-naphthoic acid, 1-hydroxy-4-phenylcarbonylmethoxy-2-naphthoic acid or 1-hydroxy-4-carbonylmethoxy-2-naphthoic acid. The thus obtained naphthoic acid is converted according to an ordinary procedure into a phenyl ester or acid chloride, which is then rected directly with a corresponding amine at an elevated temperature, or with said amine in a solvent such as benzene in the presence of pyridine or sodium carbonate at room temperature or at an elevated temperature, whereby the naphthol type coupler can be obtained. Alternatively, the said coupler may be obtained by reacting a free acid with a corresponding amine at room temperature in the presence of dicyclohexyl carbodiimide.

A phenol type coupler may be obtained in the same manner as above from a 1,4-dihydroxybenzene derivative. If necessary, however, one of the hydroxy groups of the starting 1,4-dihydroxybenzene derivative is blocked by acylation with, for example, an acetyl or benzoyl group, thereafter converted into a corresponding carbonylmethoxy derivative, and then hydrolyzed by use of an acid such as hydrochloric or sulfuric acid or an alkali such as sodium hydroxide or potassium hydroxide, whereby a corresponding coupler or an intermediate thereof can be obtained. In case the acylation is not desirable, the coupler may be synthesized in such a manner that one of the hydroxyl groups of the starting material is benzylated to a benzyloxy group, which is then subjected to the same reaction as above and thereafter to reduction with hydrogen gas according to an ordinary procedure to remove the benzyl group.

Typical procedures for synthesizing the couplers of the present invention are explained in detail below with reference to synthesis examples.

SYNTHESIS EXAMPLE 1

Into a solution of 0.05 mole of 1,4-dihydroxy-2-naphthoic acid in 70 ml. of DMF were dropped, with introduction of nitrogen gas, 10 ml. of a 40% aqueous sodium hydroxide solution and then a solution of 0.05 mole of phenacyl bromide in 10 ml. of DMF, and the resulting mixture was reacted with stirring at 40° C. for 3 to 4 hours. After completion of the reaction, the reaction liquid was poured into ice-hydrochloric acid to deposit crystals, which were then recovered by filtration and recrystallized from acetonitrile to obtain 1-hydroxy-4-benzoylmethoxy-2-naphthoic acid having having a melting point of 190° C. 0.01 Mole of the thus obtained compound and 0.01 mole of N-($\delta$-2,4-di-tert-amylphenoxy)butylamine were dissolved in 60 ml. of dehydrated dioxane and added with 0.01 mole of dicyclohexyl carbodiimide. The resulting mixture was reacted with stirring at room temperature for 2 hours. After completion of the reaction, the reaction liquid was subjected to filtration, and the filtrate was vaporized under reduced pressure. The residue was charged with n-hexane to deposit crystals, which werethen recoveredby filtration and recrystallized from benzene-n-hexane to obtain a compound having a melting point of 120° to 121° C. (yield 75%). From the measurement of its elementary analysis values and the like, the thus obtained compound was found to be the coupler (1).

SYNTHESIS EXAMPLE 2

Into a solution of 0.05 mole of 1,4-dihydroxy-2-naphthoic acid in 70 ml. of DMF were dropped, with introduction of nitrogen gas, 10 ml. of a 40% aqueous sodium hydroxide solution and then a solution of 0.05 mole of chloroacetic acid anilide in 15 ml. of DMF, and the resulting mixture was reacted with stirring at 50° C. for 3 to 4 hours. After completion of the reaction, the reaction liquid was poured into ice-hydrochloric acid to deposit crystals, which were then recovered by filtration and recrystallized from acetonitrile to obtain 1-hydroxy-4-anilinocarbonylmethoxy-2-naphthoic acid having a melting point of 215° C. 0.01 Mole of the thus obtained compound and 0.01 mole of N-($\delta$-2,4-di-tert-amylphenoxy)butylamine were dissolved in 60 ml. of dehydrated dioxane and added with 0.01 mole of dicyclohexyl carbodiimide. The resulting mixture was reacted with stirring at 50° to 60° C. for 30 minutes. After completion of the reaction, the reaction liquid was subjected to filtration to remove the by-produced dicyclohexylurea, and then the filtrate was vaporized under reduced pressure. Subsequently, the residue was charged with n-hexane to deposit crystals, which were then recovered by filtration and recrystallized from benzene to obtain a compound having a melting point of 165° to 166° C. (yield 80%). From the measurement of its elementary analysis values and the like, the thus obtained compound was found to be the coupler (2).

SYNTHESIS EXAMPLE 3

Into a solution of 0.05 mole of 1,4-dihydroxy-2-naphthoic acid in 70 ml. of DMF were dropped, with introduction of nitrogen gas, 10 ml. of a 40% aqueous sodium hydroxide solution and then a solution of 0.05 mole of p-nitrophenyl chloroacetate ester in 15 ml. of DMF, and the resulting mixture was reacted with stirring at 60° C. for 3 to 4 hours. After completion of the reaction, the reaction liquid was poured into ice-hydrochloric acid to deposit crystals, which were then recovered by filtration and recrystallized from acetonitrile to obtain 1-hydroxy-4-p-nitrophenoxycarbonyl-methoxy-4-naphthoic acid having a melting point of 202° C. 0.01 Mole of the thus obtained compound and 0.01 mole of N-($\delta$-2,4-di-tert-amylphenoxy)butylamine were dissolved in 60 ml. of dehydrated dioxane and added with 0.01 mole of dicyclohexyl carbodiimide, and the resulting solution was reacted at 50° to 60° C. for about 30 minutes. After completion of the reaction, the reaction liquid was subjected to filtration to remove the by-produced dicyclohexylurea, and then the filtrate was vaporized under reduced pressure. Subsequently, the residue was charged with n-hexane to deposit crystals, which were then recovered by filtration and recrystallized from benzene to obtain a compound having a melting point of 155° to 156° C. (yield 55%). From the measurement of its elementary analysis values and the like, the thus obtained compound was found to be the coupler (4).

SYNTHESIS EXAMPLE 4

0.01 Mole of 1-hydroxy-4-nitrophenoxycarbonylmethoxy-2-naphthoic acid, which is the intermediate obtained in Synthesis Example 3, and 0.01 mole of n-dodecylamine were dissolved in 60 ml. of dehydrated dioxane. The resulting solution was charged with 0.01 mole of dicyclohexyl carbodiimide and then reacted at 50° to 60° C. for 30 minutes. After completion of the reaction, the reaction liquid was subjected to filtration, and the filtrate was vaporized under reduced pressure. Subsequently, the residue was charged with n-hexane to deposit crystals, which were then recovered by filtration to obtain a nitro body. This nitro body was reduced according to an ordinary procedure by use of zinc and hydrochloric acid to obtain an amino body. The amino body was diazotized, and was coupled in an alkaline state with a disodium salt of 1-hydroxynaphthalene-3,6-disulfonic acid to obtain a compound having a melting point of more than 300° C. (yield 65%). From the measurement of its elementary analysis values and the like, the thus obtained compound was found to be the coupler (7).

SYNTHESIS EXAMPLE 5

Into a solution of 0.05 mole of 1,4-dihydroxy-2-naphthoic acid in 70 ml. of DMF were dropped, with introduction of nitrogen gas, 10 ml. of a 40% aqueous sodium hydroxide solution and then a solution of 0.05 mole of ethyl bromoacetate ester was added dropwise, and the resulting mixture was rected with stirring at 60° C. for 3 to 4 hours. After completion of the reaction, the reaction liquid was poured into ice-hydrochloric acid to deposit crystals, which were then recovered by filtration and recrystallized from acetonitrile to obtain 1-hydroxy-4-ethoxycarbonyl-methoxy-2-naphthoic acid having a melting point of 192° to 193° C. 0.01 Mole of the thus obtained compound and 0.01 mole of N-($\delta$-2,4-di-tert-amylphenoxy)butylamine were dissolved in 60 ml. of dehydrated dioxane, and the resulting solution was incorporated with 0.01 mole of dicyclohexyl carbodiimide and then rected at 50° to 60° C. for 30 minutes. After completion of the reaction, the reaction liquid was subjected to filtration under reduced pressure. Subsequently, the residue was charged with n-hexane to deposit crystals, which were then recovered by filtration and recrystallized from n-hexane to obtain a compound having a melting point of 92° to 93° C. (yield 75%). From the measurement of its elementary analysis values and the like, the thus obtained compound was found to be the coupler (11).

Thus, various couplers can be synthesized according to the above-mentioned synthesis procedures. Among many couplers thus synthesized, the couplers exemplified previously were measured in elementary analysis values to obtain the results shown in the following table:

| Coupler No. | Calculated | | | Found | | |
|---|---|---|---|---|---|---|
| | C | H | N | C | H | N |
| 1 | 76.81 | 7.77 | 2.30 | 76.72 | 7.79 | 2.64 |
| 2 | 74.97 | 7.74 | 4.48 | 74.67 | 8.05 | 4.94 |
| 3 | 74.85 | 7.57 | 2.24 | 74.94 | 7.64 | 2.29 |
| 4 | 69.83 | 6.91 | 4.18 | 69.49 | 7.13 | 4.20 |
| 5 | 72.69 | 8.07 | 4.99 | 72.43 | 8.21 | 5.07 |
| 6 | 71.04 | 7.31 | 2.63 | 70.70 | 7.41 | 2.72 |
| 7 | 55.96 | 4.92 | 4.77 | 55.63 | 5.30 | 4.70 |
| 8 | 73.33 | 8.13 | 4.58 | 73.55 | 8.25 | 4.46 |
| 9 | 73.87 | 7.97 | 4.10 | 73.97 | 7.98 | 4.41 |
| 10 | 65.09 | 6.10 | 5.95 | 64.75 | 6.52 | 5.70 |
| 11 | 72.76 | 8.21 | 2.42 | 72.43 | 8.34 | 2.41 |
| 12 | 71.27 | 8.03 | 7.12 | 71.01 | 8.06 | 7.15 |
| 13 | 73.57 | 7.19 | 4.34 | 73.59 | 7.07 | 4.35 |
| 14 | 71.78 | 7.50 | 3.72 | 71.95 | 7.35 | 3.51 |
| 15 | 68.39 | 8.83 | 4.09 | 68.60 | 8.98 | 4.33 |
| 16 | 57.78 | 7.19 | 4.65 | 57.53 | 7.31 | 4.43 |
| 17 | 67.02 | 6.75 | 3.91 | 66.83 | 7.02 | 3.76 |
| 18 | 66.90 | 5.08 | 5.04 | 67.22 | 5.35 | 4.94 |
| 19 | 67.96 | 5.46 | 6.89 | 67.71 | 5.45 | 6.72 |
| 20 | 70.77 | 4.59 | 7.50 | 71.05 | 4.63 | 7.73 |
| 21 | 58.37 | 4.61 | 4.00 | 58.69 | 4.37 | 4.24 |
| 22 | 72.97 | 7.38 | 2.18 | 73.15 | 7.64 | 2.15 |
| 23 | 73.21 | 7.72 | 6.58 | 73.57 | 7.92 | 6.74 |

The couplers of the present invention which are obtained in the above-mentioned manner are higher in color-forming speed at the time of color development than conventional 4-equivalent cyan couplers, as mentioned previously, and than 2-equivalent couplers of such a type that aryloxy groups such as phenoxy or nitrophenoxy groups, for example, have been used as split-off groups, or that split-off groups such as acetoxy or benzoyloxy groups have been linked through ester bonds. Further, even when compared with conventional couplers similar in structure, the couplers of the present invention are more easily dispersible in photographic protective colloids e.g. gelatin. Among the couplers of the present invention, those of the oil-soluble type show excellent solubility in solvents; those of the type having hydrophilic groups show excellent characteristics for adoption of Fischer dispersion method; and those of the so-called Kodachrome type have such advantages as can be easily incorporated into color developers. By virtue of such characteristic properties, the couplers of the present invention have such advantages that when they are incorporated into the photosensitive layers of photographic materials, like in thecase of the so-called internal type couplers, the photosensitive layers can be madethinner to enhance the resulting color images in sharpness and the like, show no detrimental interactions with the color developing agents used, and can inhibit the photographic materials from color stain and the like because of their being high in reactivity with the developing agents. Furthermore, dyes formed by use of the the couplers of the present invention have excellent color-absorbing characteristics, as mentioned previously.

The couplers of the present invention which have such characteristic properties as mentioned above ca n be used for various applications by proper combination of matrix structures with split-off groups. That is, the couplers, in which the cyan coupler residues have water-soluble groups such as sulfonic or carboxylic groups, shows a diffusibility in a gelatin binder while those, in which the split-off groups having bond groups according to the present invention are diffusible, can be utilized as diffusible couplers, which can be used for the Kodachrome type color photography. For example, the coupler (18) exemplified previously is acoupler of this kind.

The couplers, in which the cyan coupler residues are diffusible and the split-off groups have diffusion-inhibiting long-chain aliphatic hydrocarbon residues such as octadecyl groups, are non-diffusible. However, the coupler, in which the cyan coupler residues and the split-off groups have been linkd at the active points with such a proper degree of said non-diffusibility as being diffusible on the whole, may also be used for the Kodachrome type photography, like in the case of the couplers of the above-mentioned type.

Preferably couplers for use in the Kodachrome type photography are, for example, the couplers (18), (19), (20) and (21).

As is well known, the Kodachrome type photography is such technique that a diffusible coupler is incorporated into a color developer, and a photographic material containing no coupler, particularly a black-and-white silver halide photographic material (designed for the Kodachrome type photography), is exposed to light and then developed with said color developer, whereby the color developing agent and the diffusible coupler penetrate into the photographic material and react with each other in the presence of silver halide having a development center to form a dye, with the result that a dye image is finally formed. A multicolor image is formed, in general, by developing the photographic material successively with different color developers containing different couplers (e.g. cyan, magenta and yellow couplers).

Such color developers may contain, in addition to color developing agents and couplers, various photographic additives which are usually used as components of color developers such as alkali metal sulfites, carbonates, bisulfites, bromides, iodides, etc. A typical composition of this kind of developers is as follows:

| Composition of the color developer: | |
|---|---|
| Color developing agent | 1–5 g. |
| Anhydrous sodium sulfite | 1–3 g. |
| Anhydrous sodium carbonate | 10–60 g. |
| Potassium bromide | 0.5–1.5 g. |
| Coupler | 1–3 g. |
| Water to make | One liter |

When used in color developers, the couplers of the present invention, particularly those which are preferable for Kodachrome type photography, are not only more easily soluble in the color developers than conventional couplers bur also exhibit such excellent characteristics as mentioned previously.

Among the couplers of the present invention, those in which the cyan coupler residues are diffusible and the split-off groups are also diffusible, but which are non-diffusible totally as couplers; those in which the cyan coupler residues are non-diffusible and the split-off groups are diffusible, and which are non-diffusible totally as couplers; and those in which the cyan coupler residues are non-diffusible and the split-off groups are diffusible, and which are diffusible totally as couplers, are suitable for use in the diffusion transfer process.

In order to impart diffusibility to individual groups, there may be adopted such procedure as to select, for example, low molecular weight groups and/or to introduce water-soluble groups, e.g. such sulfonic acid groups as mentioned previously, while in order to impart non-diffusibility to individual groups, there may be adopted such procedure as to introduce long-chain aliphatic hydrocarbon residues and/or to select relatively high molecular weight groups.

Even in the case of couplers, in which the cyan coupler residues are diffusible and the split-off groups are also diffusible, the said coupler may be usedin the diffusion transfer process so far as the chemical structural parts, which do not take part in image formation at the time of color development, are non-diffusible. For example, when hydroquinone residues, resorcinol residues or the likes are introduced through or not through a suitable bond group into either of the cyan coupler residues and the split-off groups, the couplers can effectively be used in the diffusion transfer process. This procedure can be applied also to couplers which are different in type of combination in diffusibility of the cyan coupler residues with the split-off groups.

As methods applicable to the diffusion transfer process, there are an image formation method which utilizes a cyan dye formed by the reaction of the cyan coupler residue with the color developing agent, and an image formation method which utilizes a split-off group moiety released at the time of color development. In the former case, the resulting cyan dye is diffusible, while in the latter case, the compound, which is obtained by the release of the split-off group from the active point of the coupler, is required to be diffusible. In case the said released compound is desired to be utilized, the said compound should have been colored and contain, for example, an azo dye or the like dye moiety. A split-off group of this type is represented by the general formula (VII),

—OCH$_2$CO-D        (VII)

wherein D is a dye residue. In the general formula (VII), the dye residue is preferably a monovalent residue of a dye having preferably water-soluble groups such as an azo, azomethine, indoaniline, indophenol or anthraquinone dye.

Couplers suitable for use in the diffusion transfer process are, for example, the couplers (7), (10), (17) and (17) exemplified previously.

As is well known, the diffusion transfer process is such a technique that the combination of a photographic material with an image-receiving material is used, the photographic material is exposed to light, and then superposed on the image-receiving material at the time of development to form an image on the image-receiving material. That is, according to the diffusion transfer process, there is used the combination of, for example, a coupler-containing silver halide photographic material with an image-receiving material having an image-receiving layer, which has been formed on a support while sub layer, inter layer and the like layer between the two. After exposing the silver halide photographic material, the photosensitive layer of the silver halide photographic material is superposed on the image-receiving layer of the image-receiving material, sometimes through a protective layer, and a color developer is infiltrated into the space between the two to develop the photographic material, thereby forming a dye in the photosensitive layer. Subsequently, the dye is transferred by diffusion to the image-receiving layer, and finally the image-receiving material is peeled off from the photographic material to form a dye image on the image-receiving material. Various processes have heretofore been known as such diffusion transfer type processes. For example, there is a process in which a photograhic material and an image-receiving material are formed into an assembly to omit the step of superposing the photographic material on the image-receiving material and the step of peeling the image-receiving material from the photographic material. In case, in said process, boundary layers between the image-receiving material and the photographic material or layers adjacent to said layers are opaque, the support of the photographic material is to be transparent and the assembly is to be exposed from the support side of the photographic material. On the other hand, in case the boundary layers or layers adjacent thereto are substantially transparent, at least one of said layers should be made opaque at a stage after exposure, e.g. at the time of color development, so that the finally obtained image is not affected by the image in the photograhic material. This kind of assembly is such that at least the support of the image-receiving material of the photographic and image-receiving materials should be transparent, and the assembly is to be exposed from the transparent support side. After exposure of the assembly, a color developer is infiltrated in the boundary between the photographic material and the image-receiving material, or in the vicinity thereof, to form an image in the image-receiving layer.

Alternatively, there is such diffusion transfer type process that a color developer has previously been incorporated into an image-receiving material, and the development and transfer treatments are carried out by merely superposing a photographic material on the image-receiving material.

In any of such diffusion transfer type processes, the coupler of the present invention is effectively used. Generally, the coupler is incorporated into a photosensitive layer, preferably a silver halide photosensitive layer, and is used ordinarily in a proportion of about 0.07 to 0.7 mole, preferably 0.1 to 0.4 mole per mole of the silver halide.

The coupler of the type known as the so-called coupled is previously incorporated into a photographic material, particularly a silver halide photographic material. In order to avoid the influence on other layers, however, the coupler is preferably non-diffusible. For this purpose, there may also be used effectively any of the aforesaid non-diffusible couplers for diffusion transfer. Preferably, the coupler is one in which the cyan coupler residue is non-diffusible and the split-off group may be diffusible or non-diffusible.

Preferable as the coupler of this type are the couplers (1), (2), (3), (4), (5), (6), (7), (8), (9), (10), (11), (12), (13), (14), (15), (22) and (23).

Among these couplers, some are substantially colorless and are couplers of the general type which, when subjected to color development, react with oxidation products of color developing agents to form dyes, while the others are colored couplers and are preferably used for the so-called masking type color compensation. For example, the couplers (7) and (10) are preferable couplers for the masking type color compensation. The masking type color compensation is carried out in such a manner that at the time of color development, the color of the colored coupler itself disappears or is removed out of the system of the photographic material and, at the same time, a cyan dye is formed by reaction with the color developing agent, and thus the color of the colored coupler itself is utilized for compensation. Generally, this kind of colored coupler is used in combination with a substantially colorless coupler.

The couplers are roughly divided, depending on their having hydrophilic or oleophilic groups in the molecules, into those of the so-called Fischer dispersion type which, at the time of incorporation into photosensitive layers for example, are formed into alkali solutions and incorporated into coating compositions for the photosensitive layers, and those of the so-called protect type which are dissolved in coupler solvents and incorporated into said coating compositions. Typical as the former type couplers are the couplers (14) and (15) exemplified previously. When dispersion procedures suitable for their types are adopted, the couplers of the present invention show, as mentioned previously, more excellent solubility than conventional couplers to result in such advantages that high density dye images are formed, the layers are made higher in transparency, and the images are enhanced in resolution.

At the time of incorporation into photosensitive materials, the couplers of the present invention are used in a proportion of about 0.07 to 0.7 mole, preferably 0.1 to 0.4 mole, per mole of silver halide. However, for masking type color compensation or for enhancement in properties of other couplers, the couplers are used in a proportion of about 0.01 to 0.1 mole, preferably about 0.03 to 0.07 mole, per mole of silver halide.

As mentioned above, the couplers of the present invention can be used for various purposes, and show excellent characteristics in individual uses.

The couplers of the present invention can be applied to various photosensitive materials, preferably light-sensitie silver halide photographic materials of various types such as, for example, silver halide photographic materials used in the aforesaid diffusion transfer processes, negative photographic materials, reversal photographic materials, positive photographic materials, direct positive type photographic materials, and silver halide photographic materials for specific uses such as, for example, for printing, X-rays, high resolution, infrared and ultraviolet.

Silver halides used in the said silver halide photographic materials are silver chloride, silver iodide, silver iodobromide, silver chlorobromide, silver chloroidobromide and the like. These silver halides are prepared, according to the kinds of photographic materials, by various processes such as neutral process, ammonia process, etc., and by various procedures such as simultaneous mixing, conversion, etc. In case the silver halides are mixed silver halides, the mixing proportions of two or more silver halides are properly selected. For example, in the case of silver halides of the type relatively low in sensitivity and fine in particle size, the main component is silver chloride, while in the case of silver halides of the type relatively high in sensitivity, the content of silver chloride becomes small, in general.

As silver halides used for the direct positive type photographic material, there are those of the Harschel reversal type, solarization type, etc. To these silver halides, proper fog is previouslyimparted either optically or chemically, in general. Further, these silver halides are chemically sensitized with active gelatin; sulfur sensitizer, e.g. allylthio carbamide, thiourea and cystine; selenium sensitizer; reduction sensitizer e.g. stannous salts and polyamines; and noble metal sensitizers, e.g. gold sensitizers which concretely are potassium aurithiocyanate, potassium chloroaurate and 2-aurosulfobenzothiazole methachloride, or sensitizers of water-soluble salts of ruthenium, rhodium and iridium which concretely are ammonim chloropalladate, potassium chloroplatinate and sodium chloropalladide (some of these act as sensitizer or antifoggants depending on their amounts). These may be used either singly or in the form of suitable mixtures (e.g. mixtures of gold sensitizers with sulfur sensitizers, or mixtures of gold sensitizers with selenium sensitizers).

Further, the silver halides can be optically sensitized to a desired wavelength area, using either one or more (e.g. supersensitization) of cyanine or merocyanine dyes such as, for example, non-methine, monomethine, dimethine and trimethine dyes.

In order to constitute photosensitive layers, the silver halides are used in the form of dispersions in proper protective colloids. As the protective colloids to be used to constitute the photosensitive layers and other layers, e.g. inter layers, protective layer, filter layer, image-receiving layers and pH controlling layer (which is used below the image-receiving layer for example), these are used gelatin, in most cases, and colloidal albumin, cellulose derivatives, and polyvinyl compounds (e.g. polyvinyl alcohols) and the like synthetic resins. These may be used either singly or in combination of two or more members. Further, an acetyl cellulose having an acetyl content of about 19 to 26% or a water-soluble ethanolamine cellulose acetate may also be used in combination therewith.

As supports for the photographic materials, there are used papers, laminates (e.g. laminates of polyethylene with papers), and films or sheets formed from glass, cellulose acetate, cellulose nitrate, polyesters, polycarbonates, polyamides, polystyrenes or polyolefins. For the purpose of improvement in adhesion to individual layers, the said supports may be subjected to various hydrophilic and the like surface treatments such as, for example, saponification treatment, corona discharge treatment, subbing treatment, setting treatment, etc.

A photographic material is constructed by at least a support and a photosensitive material provided thereon, but is generally composed of three or more layers by providing proper layers at various positions, according to the purpose of application of the photographic material. Further, a color photographic material, for example, may have two or more photosensitive layers sensitized to different wavelength areas, and the said photosensitive layers may contain couplers capable of forming different colors.

The coupler of the present invention forms a cyan dye when the cyan coupler residue moiety is utilized, and hence is used, in general, in a color photographic material in combination with 2- or 4-equivalent type couplers such as a magenta coupler, e.g. at 5-pyrazolone, and a yellow coupler having an active methylene group interposed between two carbonyl groups, and, in the case of an internal photographic material, the individual couplers are incorporated into photosensitive layers having suitable sensitive wavelength areas. Further, in a pseudo-color photographic material, the coupler of the present invention may be used either singly or in combination with cyan couplers of the same kind. In this case, the relation between sensitive wavelength area and coupler does not coincide with that in an ordinary color photographic material.

A photosensitive layer having a certain sensitive wavelength area may be composed of two or more layers, which may be different in sensitivity. Further the couplers to be incorporated into the individual layers may, for example, be 2- and 4-equivalent couplers which form the same color but are different in type. This procedure may be carried out for the purpose of enhancing the sensitivity for further improvement in resolution, for example.

Further, the coupler of the present invention can be used in combination with other 2- or 4-equivalent couplers, as mentioned above. In this case, there may be ued as the 2-equivalent coupler a so called colored coupler (e.g. a coupler in which an azo group-containing split-off group has linked to the active point of the coupler), or a so-called DIR coupler (a coupler yielding a coloration inhibitor at the time of development, e.g. a coupler in which a thio group-containing split-off group has linked to the active point of the coupler).

The photographic material may contain, according to its application purpose, various photographic additives in the photosensitive layer and/or other layers (e.g. inter layer, sub layer, filter layer, protective layer, image-receiving layer, etc.). Examples of said photographic additives include stabilizers such as mercury compounds, triazoles, azaindenes and zinc or cadmium salts; sensitizers such as quaternary ammonium salts and polyethylene glycols; film property-improvers such as glycerin, dihydroxyalkanes, ethylenebis-glycolic acid esters and polymer dispersions; hardeners such as formaldehyde, halogen substituted fatty acids, disulphonic acid chloride, bisaziridines and ethylenedimines; vehicles such as saponin, lauryl or oleyl monoethers of polyethylene glycols and sulfated and alkylated polyethylene glycol salts; organic solvents such as coupler solvents (high boiling point organic solvents and/or low boiling point organic solvent, more concretely dibutyl phthalate, tricresyl phosphate, acetone, methanol, ethanol, ethylene cellosolve, etc.); and so-called DIR compounds which yield coloration inhibitors and, at the same time, form substantially colorless compounds at the time of color development. In addition therto, there are used either singly or in combination such various photographic additives as antistatic agents, defoaming agents, ultraviolet absorbers, fluoroescent brighteners, slip-preventors, matting agents, anti-halation or anti-irradiation agents, etc.

Further, the image-receiving material, which is different from the photographic material and which is used in combination with such photographic material in the diffusion transfer process, has at least an image-receiving layer on such photographic support as mentioned previously, and, if necessary, has protective layer, sub layer pH-controlling layer etc. These layers contain as layer-forming components such protective colloids as mentioned previously, and, if necessary, may be incorporated with the above-mentioned various photographic additives. For example, the image-receiving layer desirably contains, in order to prevent the re-diffusion or oozing-out of diffusible dyes from the photosensitive layer at the time of color development, compounds having properties of capturing the dyes or compounds capable of depriving the dyes of their diffisibility. These compounds may alternatively be incorporated into layers adjacent to the image-receiving layer. Typical examples of the said compounds are such polymers of vinyl methyl ketones as disclosed in U.S. Pat. No. 2,882,156, such mordants as disclosed in U.S. Pat. Nos. 3,271,148 and 3,271,147, and pH controlling agents such as inorganic and organic acids.

On the other hand, the color developer used for color development of the photographic material is a solution containing a color developing agent as active ingredient, as mentioned previously. Typical as such color developing agent are those of the p-phenylenediamine type and include, for example, diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)toluene, N-ethyl-N-$\beta$-methanesulfonamidoethyl-3-methyl-4-aminoaniline sulfate, N-ethyl-N-$\beta$-methanesulfonamidoethyl-4-aminoaniline and 4-N-ethyl-N-$\beta$-hydroxyethyl-aminoaniline. These color developing agents are used either singly or in the form of a mixture of two or more members, and, if desired, may be used in combination with a black-and-white developing agent such as hydroquinone, for example. Further, the color developer contains, in general, an alkali agent such as, for example, sodium hydroxide, ammonium hydroxide, sodium carbonate, sodium sulfate or sodium sulfite, and may contain various additives such as, for example, an alkali metal halide, e.g. potassium bromide, a restrainer such as citrazinic acid, etc. In a certain diffusion transfer process, it is an ordinary practice that the color developer is previously incorporated into the image-receiving material. In this kind of technique, however, it is also possible to adopt such procedure that the color developing agent and the alkali agent are used separately to incorporate only the alkali agent or the color developing agent into the image-receiving material, and the development is carried out by use of other solution.

The coupler of the present invention reacts with an oxidation product of color developing agent which is formed at the time of development of silver halide with such color developer to form a cyan dye. Depending on the kind of the coupler used, other dyes (including cyan dye) may be formed.

After such color development treatment as above, silver halide or developed silver in the photographic material is removed out of the system. In this case, a treatment using a fixing solution, the combination of a bleaching solution with a fixing solution, or a bleach-fixing solution is carried out in combination with various other treatments such as, for example, water-washing, stopping and stabilization treatments. As the fixing component is used a solvent for silver halide, such as sodium thiosulfate or ammonium thiosulfate. As the bleaching component is used potassiun ferricyanide, ferric ammonium ethylenediamine tetraacetic acid or a sodium salt thereof.

The present invention is so constructed as mentioned above, and the couplers of the present invention are more excellent in photographic properties than conventional 2-equivalent couplers, as mentioned previously.

The present invention is illustrated in further detail below with reference to examples, but the scope of the invention is not limited to the examples.

EXAMPLE 1

10 Grams of each of such couplers as shown in Table 1 was completely dissolved at 60° C. in a mixed solvent comprising 20 ml. of dibutyl phthalate and 60 ml. of ethyl acetate. This solution was mixed with 5 ml. of a 10% aqueous solution of Alkanol B (alkylnaphthalene sulfonate, produced by Du Pont) and 200 ml. of a 5% aqueous gelatin solution, and the resulting mixture was emulsified by use of a colloid mill to form a coupler dispersion. The coupler dispersion as incorporated into 500 g. of a negative high speed gelatin-silver iodobromide emulsion (containing 6.0 mole% of silver iodide), which was then coated on a cellulose triacetate film base and dried to prepare a sample.

The thus prepared sample was exposed through an optical wedge and then developed at 20° C. for 10 minutes with a color developer of the following composition;

| Composition of the color developer: | |
|---|---|
| N-Ethyl-N-β-methanesulfonamidoethyl-3-methyl-4-aminoaniline sulfate | 5.0 g. |
| Anhydrous sodium sulfite | 2.0 g. |
| Sodium carbonate (monohydrate) | 50.0 g. |
| Potassium bromide | 1.0 g. |
| Sodium hydroxide | 0.55 g. |
| Benzyl alcohol | 4.0 ml. |
| Water to make | One liter |

Subsequently, the developed sample was subjected to ordinary stopping and fixing treatments, washed with water for 10 minutes, and then bleached at 20° C. for 5 minutes with a bleaching solution of the following composition:

| Composition of the bleaching solution: | |
|---|---|
| Potassium ferricyanide | 100 g. |
| Potassium bromide | 50 g. |
| Water to make | One liter |

The sample was then washed with water for 5 minutes, and thereafter fixed at 20° C. for 5 minutes with a fixing solution of the following composition:

| Composition of the fixing solution: | |
|---|---|
| Sodium thiosulfate (pentahydrate) | 250 g. |
| Water to make | One liter |

The sample was again washed with water for 25 minutes and then dried.

The thus treated sample was measured in photographic properties to obtain the results shown in Table 1.

Table 1

| Sample No. | Coupler used | Relative speed | Gamma ($\gamma$) | Maximum density ($D_{max}$) | Absorption maximum ($\lambda_{max}$) | Image Light fastness | Image Humidity fastness |
|---|---|---|---|---|---|---|---|
| 1 | Coupler (2) | 130 | 1.15 | 2.22 | 700 mμ | 90% | 74% |
| 2 | Coupler (11) | 142 | 1.22 | 2.36 | 700 mμ | 92% | 75% |
| 3 | Control coupler (1) | 100 | 1.00 | 1.95 | 700 mμ | 90% | 68% |

In Table 1, the relative speed is a relative value measured by assuming as 100 the speed of the sample 3 containing the control coupler (1). The control coupler (1) is a compound having such structure as shown below

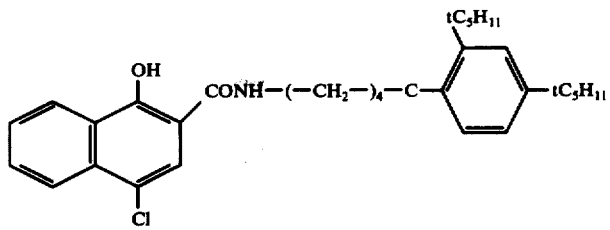

(disclosed in U.S. Pat. No. 2,474,293) The light fastness is the percentage of the residual density of each image after exposure to a xenon Fade-Ometer for 16 hours, assuming as 100 the density of the image before exposure, and the humidity fastness is the percentage of each image after incubation for 2 weeks under the conditions of 50° C. and 80% RH, assuming as 100 the density of the image before incubation.

As is clear from Table 1, the couplers of the present invention showed excellent photographic properties (high speed, excellent light and humidity fastnesses, etc.), and the samples containing the couplers of the present invention gave color images high in resolution.

The above-mentioned operation was repeated, except that the couplers (3) and (11) were replaced by the couplers (1), (9) and (12). In this case also, the couplers showed excellent properties as internal couplers like in the above.

EXAMPLE 2

10 Grams of the coupler (4) was completely dissolved at 60° C. in a mixed solvent comprising 20 ml. of dibutyl phthalate and 60 ml. of ethyl acetate. This solution was mixed with 5 ml. of a 10% aqueous solution of Alkanol B and 200 ml. of a 5% aqueous gelatin solution, and the resulting mixture was emulsified by use of a colloid mill to form a coupler dispersion. The coupler dispersion was incorporated into 500 g. of a red-sensitive high speed silver iodobromide emulsion (containing 40 mole % of silver iodide), which was then coated on a cellulose acetate film base and dried to prepare a photographic material having a stable coating film.

The thus prepared photographic material was exposed in the same manner as in Example 1, and then developed at 21° C. for 12 minutes with a developer of the following composition:

| Composition of the developer: | |
|---|---|
| Metol | 3.0 g. |
| Anhydrous sodium sulfite | 50.0 g. |
| Hydroquinone | 6.0 g. |
| Anhydrous sodium carbonate | 40.0 g. |
| Potassium bromide | 3.5 g. |
| Potassium thiocyanide | 2.0 g. |
| Water to make | One liter |

This photographic material was subjected to ordinary stopping, film-hardening and water-washing treatments, thereafter subjected to secondary exposure by use of a white light, and then color developed at 21° C. for 13 minutes with a color developer of the following composition:

| Composition of the color developer: | |
|---|---|
| N,N-Diethyl-2-methyl-p-phenylenediamine | 3.0 g. |
| Anhydrous sodium sulfite | 4.0 g. |
| Sodium carbonate (monohydrate) | 20.0 g. |
| Potassium bromide | 2.0 g. |
| Water to make | One liter |

Subsequently, the photographic material was stopped, water-washed, bleached and fixed according to ordinary procedures, washed with running water for 20 minutes and then dried to obtain a cyan positive color image excellent in transparency which had an absorption maximum at 700 m$\mu$.

From the above, it is understood that the coupler of the present invention displays excellent photographic properties even when used in a reversal type photographic material.

The above-mentioned operation was repeated, except that the coupler (4) was replaced by the coupler (23), to obtain the same excellent results as above.

EXAMPLE 3

20 Grams of each of such couplers as shown in Table 2 was dissolved in a mixed solvent comprising 20 ml. of tricresyl phosphate and 60 ml. of ethyl acetate, and the resulting solution was treated in the same manner as in Example 1 to form a coupler dispersion. This coupler dispersion was incorporated into 100 ml. of a high speed silver iodobromide emulsion, which was then coated on a film base and dried to prepare a photographic material.

The thus prepared photographic material was exposed according to an ordinary procedure, and then developed at 38° C. for 3 minutes and 15 seconds with a color developer of the following composition:

| Composition of the color developer: | |
|---|---|
| N-Ethyl-N-($\beta$-hydroxyethyl)-3-methyl 4-aminoaniline hydrochloride | 5.0 g. |
| Anhydrous sodium sulfite | 2.0 g. |
| Sodium carbonate | 50.0 g. |
| Potassium bromide | 1.0 g. |
| Sodium hydroxide | 0.55 g. |
| Water to make | One liter |

The photographic material was then bleached at 38° C. for 6 minutes with a bleaching solution of the following composition:

| Composition of the bleaching solution: | |
|---|---|
| Disodium salt of ethylenediamine tetraacetate | 40.0 g. |
| Ferric chloride | 30.0 g. |
| Sodium carbonate (monohydrate) | 20.0 g. |
| Potassium bromide | 30.0 g. |
| Water to make | One liter |

Subsequently, the photographic material was subjected to ordinary water-washing, fixing and stabilization treatments to obtain a positive image having an absorption maximum in the vicinity of 520 to 535 m$\mu$ and an excellently colored cyan dye image having an absorption maximum at 700 m$\mu$.

The thus obtained sample was measure in photographic properties to obtain the results set forth in Table 2.

In the table, the relative speed is a relative value measured by assuming as 100 the speed of the sample (6) containing the control coupler (2) of the structure shown below.

(disclosed in U.S. Pat. No. 3,034,892)

Table 2

| Sample No. | Coupler used | Relative speed | Maximum density ($D_{max}$) | Absorption maximum ($\lambda_{max}$) | Absorption maximum wavelength of masking color ($\lambda_{max}$) |
|---|---|---|---|---|---|
| (4) | Coupler (7) | 142 | 1.9 | 700 | 500 |
| (5) | Coupler (10) | 137 | 1.8 | 700 | 520 |
| (6) | Control coupler (2) | 100 | 1.6 | 700 | 500 |

In the above table, the absorption maximum of masking color is the absorption maximum due to coloration of the coupler itself.

In this example, the couplers of the present invention were used as couplers having a so-called masking type color compensation ability. As is clear from Table 2, they showed excellent photographic properties and were far more excellent in speed and density than the conventional coupler. At the same time they gave excellent dye images enhanced in sharpness.

EXAMPLE 4

The coupler (16) was incorporated according to the Fischer dispersion method into an ordinary negative high speed silver iodobromide emulsion (the amount of the coupler being 0.2 mole per mole of the silver halide). This emulsion was coated according to an ordinary procedure on a cellulose triacetate film base and then dried to prepare a sample.

The thus prepared sample was exposed and then developed at 24° C. for 3 minutes with an alkaline developer of the following composition:

| Composition of the developer: | |
|---|---|
| Sodium sulfite | 2.0 g. |
| 4-N-Ethyl-N-β-hydroxyethyl-aminoaniline | 11.0 g. |
| Water to make | One liter |

In this development, the photosensitive layer of the above-mentioned sample was closely contacted with the image-receiving layer of an image-receiving material having a dimethyl-β-hydroxyethyl-γ-stearamidopropylammonium hydrogen phosphate-containing image-receiving layer on a polyethylene coated paper. After the development, the image-receiving material was peeled off from the sample, whereby a clear cyan positive image having excellent photographic properties was formed on the image-receiving material. Thus, the coupler of the present invention had excellent properties also as a diffusion transfer coupler.

EXAMPLE 5

A solution of the coupler (18) in methanol was used to prepare color developer of the following composition:

| Composition of the color developer: | |
|---|---|
| N,N-Diethyl-2-methyl-p-phenylenediamine | 2.0 g. |
| Anhydrous sodium sulfite | 2.0 g. |
| Sodium carbonate (monohydrate) | 20.0 g. |
| Potassium bromide | 1.0 g. |
| Coupler (18) | 2.0 g. |
| Water to make | One liter |

A high speed silver iodobromide emulsion was coated on a subbed polyethylene terephthalate film to obtain a sample. This sample was exposed and then developed with the above-mentioned external color developer at 24° C. for 3 minutes. After the development, the sample was subjected to water-washing for 4 minutes, bleaching for 5 minutes, water-washing for 5 minutes, fixing for 5 minutes, water-washing for 30 minutes and drying in this order to obtain a cyan image having an absorption maximum at 700 m$\mu$ which was excellent in special absorption characteristics and in order photographic properties.

The above-mentioned operation was repeated, except that the coupler (18) was replaced by the coupler (19), to obtain an excellent dye image having an absorption maximum at 700 m$\mu$. Thus, the couplers of the present invention were useful also as Kodachrome type couplers.

EXAMPLE 6

Dispersion A:

0.15 Gram of the coupler (7) and 2.0 g of a known coupler 1-hydroxy-N-[δ-(2,4-di-tert-amylphenoxy)-butyl]-2-naphthamide were dissolved in a mixed solvent comprising 2.2 ml. of tricresyl phosphate and 6.0 ml. of ethyl acetate, and the resulting solution was treated in the same manner as in Example 1 to prepare a coupler dispersion.

Dispersion B:

A dispersion was prepared by incorporating into the dispersion A 0.20 g. of a development inhibitor-releasing type compound 2-(1-phenyl-5-tetrazolylthio)-4-[2-(2,4-di-tert-amylphenoxy)-acetamide]indanone.

Dispersion C:

A dispersion was prepared in the same manner as in the case of the dispersion B, except that the development inhibitor-releasing type compound was replaced by 0.1 g. of a development inhibitor-releasing type coupler 1-hydroxy-4-(1-phenyl-5-tetrazolylthio)-2-(2-tetradecyloxyphenyl)naphthamide.

Dispersion D:

A dispersion was prepared in the same manner as in the case of the dispersion B, except that the coupler (7) was replaced by the known control coupler (2).

These dispersions were individually incorporated into 100 ml. of a red-sensitive high speed silver iodobromide emulsion (containing 7.0 mole% of silver iodide), which was then coated on a film base and dried to prepare four photographic materials.

These photographic materials were exposed according to an ordinary procedure and then treated in the same manner as in Example 3, whereby the photographic materials B and D gave color images which were more excellent in gradation, graininess and sharpness than those formed from the photographic materials A and C. The results obtained were as set forth in Table 3.

Table 3

| Photographic material | Fog | Speed | Gamma | Graininess (RMS) | Sharpness (U 0.5) |
|---|---|---|---|---|---|
| A | 0.21 | 100 | 1.00 | 54 | 51 |
| B | 0.10 | 97 | 0.72 | 40 | 40 |
| C | 0.13 | 92 | 0.72 | 4.5 | 42 |
| D | 0.12 | 93 | 0.71 | 43 | 41 |

In the table, the RMS is a 1,000-time value of the standard deviation of variation in density value which is formed when scanned by means of a microdensitometer of 2.5 $\mu$ in circle-type scanning opening diameter; and the U 0.5 is a value of the number of space frequency at which the MT factor decreases to 50%.

What we claim is:

1. A process for forming a cyan dye image, which comprises bringing a 2-equivalent type cyan coupler into contact with exposed silver halide crystals in the presence of a phenylenediamine type developing agent for said silver halide crystals, said 2-equivalent cyan coupler having the general formula:

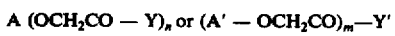

wherein A and A' each represent, at the active point of the cyan coupler, a cyan coupler residue, which has the general formula:

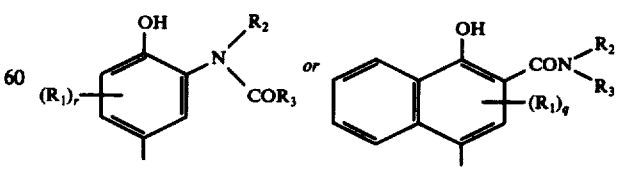

wherein $R_1$ represents a hydrogen atom, a halogen atom, a saturated or unsaturated, aliphatic or cycloaliphatic hydrocarbon group, —O—$R_4$ or —S—$R_4$ (where $R_4$ represents a said hydrocarbon group), r is 1 to 3 and q is 1 to 5 and if r or q is more than 1 the $R_1$ groups may be the same or different; and each of $R_2$ and $R_3$ independently represents a saturated or unsaturated, aliphatic or cycloaliphatic hydrocarbon group, an aryl group, a heterocyclic group or hydrogen atom or $R_2$ and $R_3$ together with the nitrogen atom to which they are attached form a heterocyclic group; Y represents a heterocyclic group, an alkoxy group, a phenoxy group, a naphthoxy group, an aliphatic hydrocarbon amino group, a heterocyclic amino group and a mercapto group, which groups also include those having substituents which are selected from halogen, nitro, hydroxyl, carboxyl, amino, sulfo, alkyl, alkenyl, aryl, heterocyclic, alkoxy, aryloxy, arylthio, arylazo, acylamino, carbamoyl, ester, acyl, acyloxy, sulfonamide, sulfamoyl, sulfonyl, morpholino, piperazyl and imidazolyl groups; Y' is an m-valent group selected from the group consisting of a heterocyclic group, an alkylenedioxy group, an arylenedioxy group, an alkylenediamino group, an arylenediamino group and a heterocyclic diamino group; wherein said Y' groups also include those having substituents which are selected from halogen, nitro, hydroxyl, carboxyl, amino, sulfo, alkyl, alkenyl, aryl, heterocyclic, alkoxy, aryloxy, arylthio, arylazo, acylamino, carbamoyl, ester, acyl, acyloxy, sulfonamide, sulfamoyl, sulfonyl, morpholino, piperazyl and imidazolyl groups; and n is 1 or 2 and m is 2.

2. A process as claimed in claim 1, wherein the cyan coupler is present in the exposed light-sensitive silver halide photographic emulsion layer of a light-sensitive color photographic material.

3. A process as claimed in claim 1, wherein the cyan coupler is present in a color developer containing the phenylenediamine type color developing agent.

4. A light-sensitive silver halide color photographic material having a support and thereon a light-sensitive silver halide emulsion layer containing the photographic 2-equivalent cyan coupler of claim 1.

5. A color developer for developing exposed light-sensitive silver halide color photographic material, which comprises a phenylenediamine type developing agent and the photographic 2-equivalent cyan coupler of claim 1.

* * * * *